United States Patent [19]

Matsuda et al.

[11] Patent Number: 5,718,923
[45] Date of Patent: Feb. 17, 1998

[54] MELT GRANULATED SUCRALFATE PREPARATIONS AND A PROCESS FOR THEIR PRODUCTION

[75] Inventors: Katsuya Matsuda; Koichi Ozawa, both of Tokyo, Japan

[73] Assignee: Chugai Seiyaku Kabushiki Kaisha, Tokyo, Japan

[21] Appl. No.: 727,643

[22] PCT Filed: Apr. 18, 1995

[86] PCT No.: PCT/JP95/00753

§ 371 Date: Oct. 15, 1996

§ 102(e) Date: Oct. 15, 1996

[87] PCT Pub. No.: WO95/28938

PCT Pub. Date: Nov. 2, 1995

[30] Foreign Application Priority Data

Apr. 26, 1994 [JP] Japan ................................. 6-088855
Aug. 11, 1994 [JP] Japan ................................. 6-189520

[51] Int. Cl.$^6$ ........................................................ A61K 9/50
[52] U.S. Cl. ........................ 424/502; 424/489; 424/472; 424/473; 424/453
[58] Field of Search .................................. 424/502, 489, 424/472, 473, 453; 604/892.1

[56] References Cited

U.S. PATENT DOCUMENTS

| 4,940,465 | 7/1990 | Theeuwes et al. | 604/892.1 |
| 5,196,405 | 3/1993 | Packman | 514/53 |
| 5,417,682 | 5/1995 | Wong et al. | 604/892.1 |

FOREIGN PATENT DOCUMENTS

WO 89/05645  6/1989  WIPO.

OTHER PUBLICATIONS

Flanders et al., "The Control of Drug Release from Conventional Melt Granulation Matrices," Drug Development and Industrial Pharmacy, vol. 13(6), pp. 1001–1022, 1987.

Kenji Ukita et al, "Preparation of Essential Oils Loaded Granule by Melt Granulation," Drug Development and Industrial Pharmacy, vol. 20(6), pp. 981–992 1994.

Masaharu Miyajima et al, "Design of Substained-Release Granules prepared by Wax Melting Method," Pharm Tech Japan vol. 8 No. 9 pp. 81–87, 1992.

Yasuo Haramishi et al, "Study on Fluidized Melt–Granulation. I. Examination of the Factors on the Factors on the Granulation[1])," Yakugaku Zasshi, vol. 111 (9) pp. 515–523, 1991.

*Primary Examiner*—Thurman K. Page
*Assistant Examiner*—William E. Benston, Jr.
*Attorney, Agent, or Firm*—Browdy and Neimark

[57] ABSTRACT

Sucralfate preparation produced by melt granulating a mixture of a comminuted sucralfate powder and a water-soluble low-melting point wax, as well as a process for producing a sucralfate preparation comprising the steps of comminuting dry sucralfate into fine particles, mixing the finely divided particles with a water-soluble low-melting point wax and heating the mixture such that the wax is melted to effect melt (adhesion) granulation of the finely divided sucralfate particles are disclosed. Compared to conventional sucralfate preparations, the thus produced sucralfate preparation has a small dispersed particle size, exhibits high capability for binding to plasma proteins and thereby achieves marked improvements in administrability and protein binding capability.

20 Claims, No Drawings

MELT GRANULATED SUCRALFATE PREPARATIONS AND A PROCESS FOR THEIR PRODUCTION

This application is a 371 of PCT/JP95/00753 filed Apr. 18, 1995

TECHNICAL FIELD

This invention relates to a sucralfate preparation and a process for its production. More particularly, the invention relates to a preparation produced by melt (adhesion) granulation of a finely divided sucralfate using a water-soluble, low-melting point wax, as well as a process for producing said preparation.

BACKGROUND ART

Sucralfate is a basic aluminum salt of sucrose sulfate, which is extensively used as a therapeutic of digestive ulcer having a substrate protein protective action (tunica mucosa ventriculi protecting action), a capability for suppressing the activity of pepsin in gastric juice and an anti-acid action. Since sucralfate is insoluble in water, the disintegration and dispersion of sucralfate preparations are important for the sucralfate to bind effectively to ulcer sites.

Conventional sucralfate preparations have been produced by mixing a yet to be dried sucralfate wet powder with additives and water and drying (spray drying) the mixture at elevated temperatures or granulating and drying the mixture. The preparations may be further mixed with additives to formulate subtilized granules or compacted into tablets.

The conventional sucralfate preparations contain so large sucralfate particles that when subtilized granules made from those preparations are administered internally, they present an off-flavor due to aluminum, graininess due to the large particle size, stickiness to the mucous membrane of the oral cavity connecting to the throat, and other minor troubles associated with administration. Making tablets of sucralfate preparations is not necessarily a preferred method since they are disintegrated into unduly large fragments upon administration.

Considering the protein binding capability which is the primary action of sucralfate, the sucralfate preparation should be divided as finely as possible in order to provide not only an increased surface area but also an enhanced dispersibility and this is effective in assuring the desired efficacy of the preparation if it is to be applied to the living body. On the other hand, sucralfate is highly cohesive and wets only poorly. This nature of sucralfate tends to become pronounced when it is finely divided and in the conventional process in which the undried sucralfate powder is mixed with additives and water, granulated and dried at elevated temperatures, the sucralfate particles agglomerate to grow in size during the evaporation of water; hence, it has been difficult to produce a sucralfate preparation that can be suspended or dispersed as fine particles on use.

DISCLOSURE OF INVENTION

The present invention has been accomplished under these circumstances and has as an object providing a sucralfate preparation that is easy to administer and which allows sucralfate to be applied in vivo in a finely divided form.

Another object of the invention is to provide a process for producing said sucralfate preparation.

In order to produce the desired sucralfate preparation, a dried sucralfate powder prepared by a prior art method is comminuted to a finer form, which is mixed with a water-soluble, low-melting point wax, with the mixture being then heated to effect melt (adhesion) granulation.

The dried sucralfate powder which is used as the starting material may typically be prepared by the method described in Japanese Patent Publication No. 11673/1969 or 16037/1969, according to which basic aluminum chloride is allowed to act on a polysulfated saccharide to form a yet to be dried sucralfate powder, which is subsequently dried, say, spray dried, at elevated temperatures. An example of the sucralfate that can be used in the invention is designated in the Pharmacopoeia of Japan.

The thus dried sucralfate powder is comminuted into a finer form. The comminuted sucralfate powder suffices to be such that at least 90% of the particles have a size not greater than 50 μm; preferably, the particles have an average size of no more than 20 μm and at least 90% of them have a size not greater than 50 μm and, more preferably, the particles have an average size of no more than 10 μm and at least 95% of them have a size not greater than 50 μm. The machine for comminuting the sucralfate powder may be of any model that can provide a particle size not greater than 50 μm and a typical example is a hammer mill.

The water-soluble, low-melting point wax to be added to the comminuted sucralfate powder is not limited in any aspects such as molecular weight and the degree of polymerization as long as it is in a powder form and has a melting point of no more than about 80° C. To mention a few examples, polyethylene glycol, polyoxyethylene-polyoxypropylene-glycol, etc., and mixtures thereof may preferably be used. More preferred water-soluble, low-melting point waxes are polyethylene glycols having melting points of 40°–70° C., such as polyethylene glycol 4000 (m.p. 53°–57° C.), polyethylene glycol 6000 (m.p. 56°–61° C.) and polyethylene glycol 20000 (m.p. 56°–64° C.).

The wax suitable for use in melt granulation must be solid at ordinary temperatures since the comminuted sucralfate powder is mixed with the yet to be molten wax in a dry powder form.

If the wax has a high melting point in excess of about 80° C., it must be heated to a high enough temperature to permit granulation, which is a problem with handling. In addition, the other components to be incorporated may be adversely affected at such high temperatures.

The water-soluble, low-melting point wax is typically used in an amount of at least 5%, preferably at least 10%, of the weight of the comminuted sucralfate powder; the wax needs to be present in a sufficient amount that the surfaces of the particles in the comminuted sucralfate powder are covered with the wax to improve their wettability. If the wax is polyethylene glycol, it is preferably added in an amount ranging from 10 to 20%.

If a hydrophobic, rather than water-soluble, wax is used, granulation in the manner specified by the invention only yields large dispersed particles and is not capable of producing a sucralfate preparation that can be suspended or dispersed as the desired fine particles.

The heating temperature to be employed in the melt granulation (also called "adhesion granulation") step of the invention process suffices to be at least equal to the melting point of the water-soluble wax to be used; preferably, heating is effected until the temperature of the formulation for the sucralfate preparation becomes 5°–10° C. higher than the melting point of the wax. Besides the water-soluble, low-melting point wax, excipients such as saccharides (e.g., lactose, mannitol and sucrose), flavoring agents, sweeteners and other conventional ingredients may be added as appropriate such that they are melt granulated together with the comminuted sucralfate powder. The sucralfate preparation produced in the invention may be immediately used as such or, alternatively, any necessary ingredients may be added to formulate subtilized granules, tablets such as chewable tablets or troches, capsules or other dosage forms.

The following examples are provided for the purpose of further illustrating the invention but are in no way to be taken as limiting.

EXAMPLE 1

A dry powder sucralfate (as specified in Pharmacopoeia of Japan, JP) was comminuted with a hammer mill at about 3,000–3,600 rpm. The resulting comminuted sucralfate powder was entirely composed of particles not larger than 50 μm, had aluminum and sulfur contents of 19.3% and 10.7%, respectively, and experienced a 10.2% loss in weight upon drying.

According to the conventional wet granulation method, a comminuted sucralfate powder (4,000 g) was mixed with a low-substitution hydroxypropyl cellulose (disintegrant, 200 g) and polyethylene glycol 1500 (100 g) and the mixture was kneaded at 400 rpm in an agitating granulator (Okada Seiko K.K.) in the presence of supplied water. Following granulation in a milling granulator (Okada Seiko K.K.), the product was dried in a ventilated dryer (Fuji Paudal K.K.) at 60° C. for 60 min.

According to melt granulation using a hydrophobic wax, a comminuted sucralfate powder (2,000 g) was mixed with a hydrogenated caster oil (Lubri Wax 101 of Freund, 400 g) and the mixture was fed into a jacketed agitating granulator (Okada Seiko K.K.), where it was granulated under agitation at 200 rpm with the Jacket being heated until the temperature of the powder layer exceeded the melting point of the wax.

According to melt granulation using a water-soluble wax, a comminuted sucralfate powder (2,000 g) was mixed with polyethylene glycol 6000 (400 g) or polyoxyethylene[105]-polyoxypropylene[5]-glycol (PEP101 of Freund, m.p. 50°–54° C.; 400 g) and the mixture was processed as described in the preceding paragraph.

Each of the samples thus prepared was measured for the dispersed particle size (i.e., the size of particles as dispersed in water) by means of a laser diffraction particle size analyzer (Nikkiso Co., Ltd.); in addition, the samples were analyzed for average size (at 50% cumulative frequency) and the proportion of particles not larger than 50 μm. The results are shown in Table 1 below.

TABLE 1

| Granulation method | Wax | Dispersed particle size Average, μm | Percent 50 μm and less |
|---|---|---|---|
| Wet granulation | Water-soluble | 23.8 | 82.9 |
| Melt granulation | Hydrophobic | 25.6 | 78.6 |
| Melt granulation | Water-soluble (polyethylene glycol) | 5.9 | 100.0 |
| Melt granulation | Water-soluble (polyoxyethylene-polyoxypropylene-glycol) | 5.2 | 100.0 |
| Comminuted sucralfate powder | | 4.4 | 100.0 |

As is clear from Table 1, the sample prepared by the conventional wet granulation method and that prepared by melt granulation using the hydrophobic wax had so large dispersed particle sizes that no preparations were obtained that could be suspended or dispersed as the desired fine particles. The samples prepared by melt granulation of sucralfate incorporating the water-soluble waxes had dispersed particle sizes approximate to the particle size of the comminuted sucralfate powder and the proportion of particles not larger than 50 μm was satisfactory at 100%.

EXAMPLE 2

A comminuted sucralfate powder (2,000 g) was mixed with Polyethylene Glycol 6000 in varying amounts of 50 g, 100 g, 200 g, 300 g and 400 g and the mixtures were fed into a jacketed agitating granulator, where they were melt granulated under agitation at 300 rpm until the temperature of the powder layer reached 65° C.

Each of the samples thus prepared was measured for the dispersed particle size by means of a laser diffraction particle size analyzer; in addition, a specific surface area measurement was conducted before and after the granulation by means of a specific surface area measuring instrument (Shimadzu Corp.) using nitrogen gas as adsorbate. The results are shown in Table 2 below.

TABLE 2

| Mixing proportions Sucralfate:polyethylene glycol | Dispersed particle size | | Specific surface area, $m^2/g$ |
|---|---|---|---|
| | Average, μm | Percent 50 μm and less | |
| 100:2.5 | 5.8 μm | 90.2% | 2.6 $m^2/g$ |
| 100:5 | 5.2 | 95.1 | 1.7 |
| 100:10 | 5.8 | 92.0 | 1.4 |
| 100:15 | 5.6 | 97.0 | 0.8 |
| 100:20 | 6.4 | 100.0 | 0.1 |
| (Comminuted sucralfate powder) | 4.4 | 100.0 | 5.1 |
| (Sucralfate of JP) | 18.6 | 86.2 | 1.6 |

As one can see from Table 2, all samples had dispersed particle sizes approximate to the particle size of the comminuted sucralfate powder and the sample prepared by adding 20% of polyethylene glycol was entirely composed of particles not larger than 50 μm.

As the sucralfate was mixed with increasing amounts of polyethylene glycol, granulation progressed and the specific surface area of particles tended to decrease. The data on specific surface area show that the sample containing 2.5% of polyethylene glycol was insufficiently granulated whereas the sample containing 20% of polyethylene glycol was granulated satisfactorily.

EXAMPLE 3

A portion (92.4 g) of the sucralfate preparation (sucralfate:polyethylene glycol=20:4) obtained in Example 2 was mixed with sucrose (7.2 g) and a flavoring agent and other ingredients (in a total of 0.4 g) in a polyethylene bag to produce subtilized granules (100 g). They had good administrability without causing any graininess.

One of the important pharmaceutical effects of sucralfate is its capability of binding to plasma proteins and this was evaluated by the following test.

To bovine serum albumin (BSA of Sanko Junyaku K.K.; 5 g), a HCl-KCl buffer solution (pH of about 1.5) was added to make a stock BSA solution weighing 1,000 ml. The subtilized granules were weighed in an amount equivalent to 30 mg of a dry sucralfate powder and dispersed in water (5 ml). The stock BSA solution (15 ml) was added to the dispersion and mixture was shaken at 37° C. for 30 min. Thereafter, a HCl-KCl buffer solution (20 ml) was added and the mixture was passed through a 0.22 μm membrane filter (Millipore) to separate the sucralfate-bound insoluble BSA. The liquid permanent was used as a sample and subjected to the following assay.

A standard solution (a dilution of the stock BSA solution) and the sample solution were each measured in 20 μl and mixed with a protein measuring reagent (Protein Assay 1→5, Biorad; 5 ml). The quantity of unbound BSA was determined from the absorbance at 595 nm as measured with a spectrophotometer (Shimadzu Corp.); BSA binding capability was calculated as the percentage of the BSA added that bound to sucralfate.

The same measurements were conducted on a commercial sample of subtilized granules (ULCERLMIN, the registered trademark of Chugai Pharmaceutical Co., Ltd.) so that the performance of the subtilized granules prepared in accordance with the invention were compared with the conventional preparation. The results of measurement of dispersed particle size and BSA binding capability are shown in Tables 3 and 4, respectively.

TABLE 3

| | Dispersed particle size | |
|---|---|---|
| | Average, μm | Percent 50 μm and less |
| Subtilized granules of invention | 5.1 | 100.0 |
| Conventional subtilized granules | 22.0 | 78.6 |

TABLE 4

| | BSA binding capability, % |
|---|---|
| Subtilized granules of invention | 69.9 (1.5) |
| Conventional subtilized granules | 47.0 (1.0) |

* The figures in parentheses are relative values.

Obviously, the subtilized granule preparation of the invention could be dispersed as particles not larger than 50 μm and showed a BSA binding capability 1.5 times as high as the conventional preparation.

EXAMPLE 4

A portion (360 g) of the sucralfate preparation (sucralfate:polyethylene glycol=20:4) obtained in Example 2 was mixed with sucrose (234.6 g), a flavoring agent and other ingredients (in a total of 2.4 g) and a lubricant (3 g) in a V-type mixer (Tsutsui Scientific Instruments Co., Ltd.) to make a powder blend for tableting. The powder was fed into a single-punch machine (Kimura Seisakusho K.K.), where it was compacted into flat, bevel edged tablets each having a diameter of 18 mm and weighing 1 g in a thickness of 3.1 mm.

The thus prepared tablets were measured for the dispersed particle size and BSA binding capability and the results are shown in Tables 5 and 6, which also show the corresponding data on a commercial sample of tablets (ULCERLMIN, the registered trademark of Chugai Pharmaceutical Co., Ltd.)

TABLE 5

| | Dispersed particle size | |
|---|---|---|
| | Average, μm | Percent of 50 μm and less |
| Invention tablet | 10.1 | 98.8 |
| Conventional tablet | 27.2 | 75.7 |

TABLE 6

| | BSA binding capability, % |
|---|---|
| Invention tablet | 65.1 (2.5) |
| Conventional Tablet | 26.0 (1.0) |

* The figures in parentheses are relative values.

Obviously, the tablets prepared in accordance with the invention had very fine dispersed particle sizes as indicated by the presence of at least 98.8% of particles not larger than 50 μm, and they showed a BSA binding capability 2.5 times as high as the conventional tablets.

INDUSTRIAL APPLICABILITY

As described on the foregoing pages, the sucralfate preparations produced by the present invention had small dispersed particle sizes and exhibited high capabilities for binding to plasma proteins as compared with the conventional preparations. Therefore, the invention is expected to make a great contribution in solving the problems associated with the administrability and protein binding capability of the sucralfate preparations produced by conventional methods. The sucralfate preparations produced by the invention have a salient feature in that they can be applied as pharmaceuticals for oral application such as subtilized granules, tablets and capsules or as pharmaceutical for external application.

We claim:

1. A sucralfate preparation produced by melt granulating a mixture of sucralfate with at least 5 wt % of a water-soluble low-melting point wax.

2. A preparation according to claim 1 which comprises sucralfate finely divided into particles at least 90% of which are not larger than 50 μm, and the water-soluble low-melting point wax.

3. A preparation according to claim 2, wherein said finely divided sucralfate has an average particle size of no more than 20 μm and at least 90% of which comprises particles not larger than 50 μm.

4. A preparation according to claim 1, wherein said wax has a melting point not higher than 80° C.

5. A preparation according to claim 4, wherein said wax is polyethylene glycol, polyoxyethylene-polyoxypropylene-glycol or a mixture thereof.

6. A process for producing a sucralfate preparation which comprises the steps of comminuting dry sucralfate into particles at least 90% of which are not larger than 50 μm, mixing the finely divided particles with a water-soluble low-melting point wax and heating the mixture such that said wax is melted thereby enabling the sucralfate particles to be granulated adhesively.

7. A process according to claim 6, wherein said water-soluble low-melting point wax is added in an amount of at least 5 wt % of the sucralfate for mixing with the latter.

8. A process according to claim 6, wherein said dry sucralfate is comminuted into particles having an average size of no more than 20 μm and at least 90% of which are not larger than 50 μm.

9. A process according to claim 6, wherein said wax has a melting point not higher than 80° C.

10. A process according to claim 9, wherein said wax is polyethylene glycol, polyoxyethylene-polyoxypropylene-glycol or a mixture thereof.

11. A process according to claim 6, wherein not only said wax but also an excipient is added.

12. A process according to claim 7, wherein said dry sucralfate is comminuted into particles having an average size of no more than 20 μm and at least 90% of which are not larger than 50 μm.

13. A process according claim 12, wherein said wax has a melting point not higher than 80° C.

14. A process according claim 8, wherein said wax has a melting point not higher than 80° C.

15. A process according to claim 14, wherein said wax is polyethylene glycol, polyoxyethylene-polyoxypropylene-glycol or a mixture thereof.

16. A process according to claim 13, wherein said wax is polyethylene glycol, polyoxyethylene-polyoxypropylene-glycol or a mixture thereof.

17. A preparation according to claim 2, wherein said wax has a melting point not higher than 80° C.

18. A preparation according to claim 17, wherein said wax is polyethylene glycol, polyoxyethylene-polyoxypropylene-glycol or a mixture thereof.

19. A sucralfate preparation formed of granules consisting essentially of finely divided sucralfate particles and an amount sufficient no less than 5% of a water-soluble low-melting point solid wax to agglomerate said finely divided particles into granules, wherein said finely divided sucralfate particles have an average particle size no greater than about 20 μm with at least 90% of said sucralfate particles having a particle size no greater than 50 μm, and wherein said water-soluble low-melting point wax has a melting point no greater than 80° C.

20. A sucralfate preparation according to claim 19, in granular form, wherein said solid wax is polyethylene glycol, polyoxyethylene-polyoxypropylene-glycol or a mixture thereof.

* * * * *